United States Patent [19]

Rust

[11] Patent Number: 5,192,690
[45] Date of Patent: Mar. 9, 1993

[54] PROCESS FOR THE ANALYTICAL DETERMINATION OF ACETYLCYANAMIDE IN URINE

[75] Inventor: Ulrich Rust, Trostberg, Fed. Rep. of Germany

[73] Assignee: SKW Trostberg Aktiegesellschaft, Trostberg, Fed. Rep. of Germany

[21] Appl. No.: 825,645

[22] Filed: Jan. 21, 1992

Related U.S. Application Data

[63] Continuation-in-part of Ser. No. 603,256, Oct. 25, 1990, abandoned, which is a continuation of Ser. No. 391,435, Aug. 9, 1989, abandoned.

[51] Int. Cl.$^5$ ............................................. G01N 33/00
[52] U.S. Cl. ................................. 436/106; 436/109; 436/20
[58] Field of Search .......................... 436/20, 106, 109

[56] References Cited

U.S. PATENT DOCUMENTS 4,692,415 9/1987 Rust ........................................ 436/20

OTHER PUBLICATIONS

Shirota et al. "N-Acetylcyanamide, the Major Urinary Metabolite of Cyanamide in Rat, Rabbit, Dog and Man" CA101(3):16971g.

*Primary Examiner*—James C. Housel
*Assistant Examiner*—Lyle A. Alexander
*Attorney, Agent, or Firm*—Kenneth P. Glynn

[57] ABSTRACT

The present invention is directed to a process for the analytical determination of acetylcyanamide in urine. It involves (a) the separating of acetylcyanamide at from a urine matrix and/or an extract which is obtained from a urine matrix by ion exchange chromatography or reverse phase high performance liquid chromatography (HPLC), and (b) detecting the acetylcyanamide at a wavelength of 220 nm. The matrix or the extract of it is cleaned by treatment with activated carbon at pH 7 to 13, and the acetylcyanamide may be extracted from the cleaned matrix or its extract at pH 0.5 to 3.5, e.g. by liquid-liquid extraction of the acetylcyanamide. This is carried out by means of water-insoluble, organic solvent such as ethyl acetate or diethyl ether.

8 Claims, 2 Drawing Sheets

PROCESS FOR THE ANALYTICAL DETERMINATION OF ACETYLCYANAMIDE IN URINE

REFERENCES TO RELATED APPLICATIONS

This application is a continuation-in-part two patent applications, as follows: U. S. copending application Ser. No. 07/603,256, filed on Oct. 25, 1990, now abandoned filed by the present inventor and entitled "Process For Analytical Determination of Acetylcyanamide", and which itself is a continuation application of 07/391,435, filed on Aug. 9, 1989, now abandoned filed by the present inventor and entitled "Process For Analytical Determination of Acetylcyanamide".

BACKGROUND OF THE INVENTION

1. Field of the Invention

The invention relates to an analytical process for the determination of acetylcyanamide in a matrix and/or in an extract which is obtained from this matrix. The method of the invention is used to determine acetylcyanamide in any desired materials or mixtures of materials, determination preferably taking place in materials of biological origin, and more specifically in urine.

2. Prior Art Statement

Acetylcyanamide may occur in the course of metabolism of cyanamide in the body of people who are being treated for therapeutic purposes with cyanamide or calcium cyanamide or who for occupational reasons come into contact with cyanamide. In the animal body is a metabolic product which is excreted, for example, by experimental animals which have been specifically fed with cyanamide. Cyanamide is being use to an increasing extent in crop cultivation. Apart from application of calcium cyanamide as field fertilizer, it is possible to use cyanamide in accordance with German Offenlegungsschrift 3,150,404 to overcome bud dormancy in vines or other fruit crops.

For environmental and health protection reasons it is desirable to develop analytical methods for the determination of acetylcyanamide in the trace range in people and in animals. Analytical methods hitherto disclosed (Shirota et alii, Drug Metabolism and Disposition 12, 337–334, (1984) are based on measurement of the radioactivity of $^{14}$C-labeled acetylcyanamide or the N-benzyl or N-(4-nitrobenzyl) derivative thereof by means of CIMS (Chemical Ionization Mass Spectrography) and UV measurement of the corresponding labeled or unlabeled compounds. Direct determination of trace amounts of unlabeled acetylcyanamide has not hitherto been described.

SUMMARY OF THE INVENTION

The present invention is directed to a process for the analytical determination of acetylcyanamide in urine. It involves (a) the separating of acetylcyanamide from a urine matrix and/or an extract which is obtained from a urine matrix by ion chromatography or reverse phase high performance liquid chromatography (HPLC), and (b) detecting the acetylcyanamide at a wavelength of 220 nm. The matrix or the extract of it is cleaned by treatment with activated carbon at Ph 7 to 13, and the acetylcyanamide may be extracted from the cleaned matrix or its extract at pH 0.5 to 3.5, e.g. by liquid-liquid extraction of the acetylcyanamide. This is carried out by means of water-insoluble, organic solvent such as ethyl acetate or diethyl ether.

BRIEF DESCRIPTION OF THE DRAWINGS

The present invention is more fully understood when the specification is taken in conjunction with the appended drawings, wherein.

DETAILED DESCRIPTION OF THE INVENTION

Figure 1:
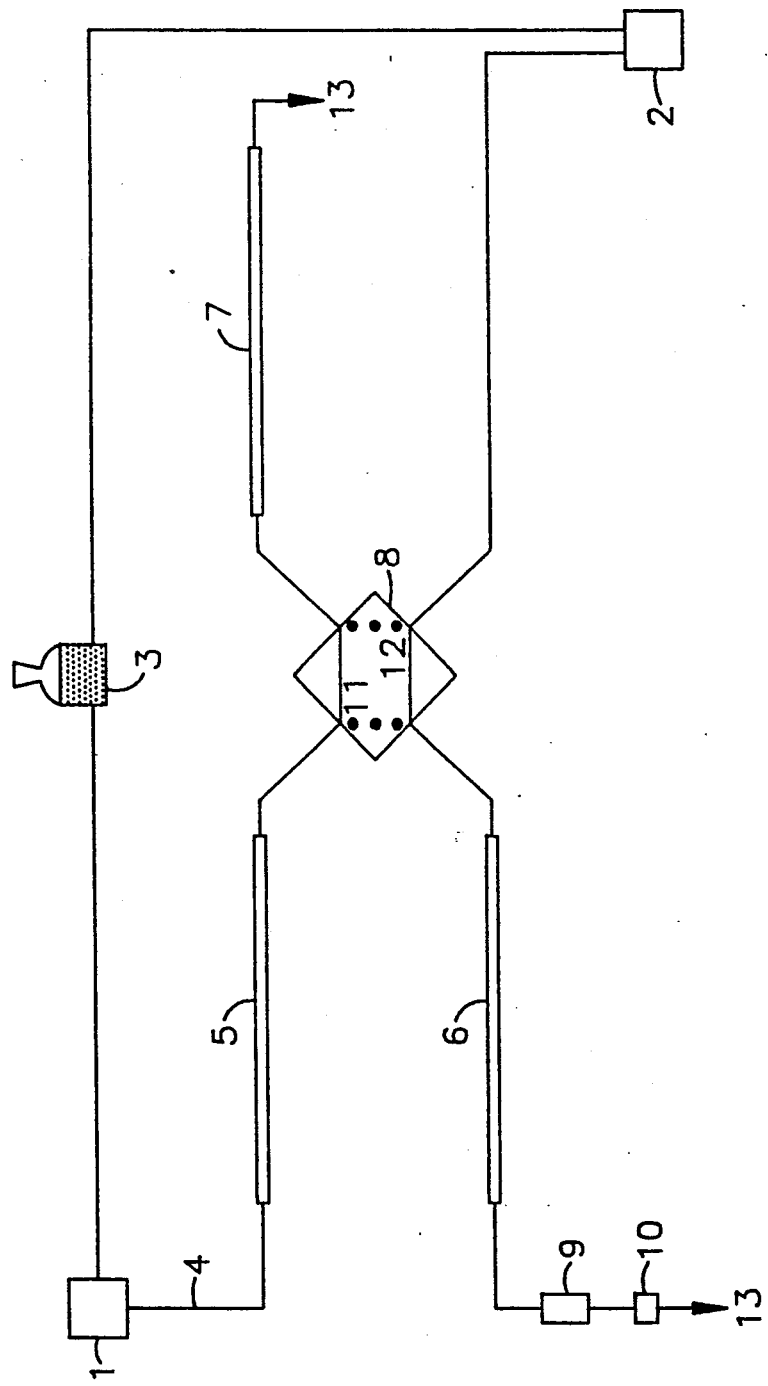
FIG. 1 illustrates a diagram of a two column separation system connected in series; and, FIG. 2 represents ion chromatograms of acetylcyanamide.

The object of the present invention is to develop a highly specific, sensitive analytical method for the quantitative determination, as well as for the detection, of acetylcyanamide, which takes account, in particular, of the metabolism of cyanamide in people and in animals and is also suitable for the determination of cyanamide in plant tissue, in microorganisms and in biological metabolic products.

The object is achieved according to the present invention, wherein acetylcyanamide in a matrix and/or in an extract which is obtained from the matrix is separated by high performance liquid chromatography (HPLC) using an ion exchange or reverse phase and is determined spectrophotometrically at a wavelength of 220 nm.

It has proven expedient to use easily accessible metabolic products for the determination of acetylcyanamide in the human and animal body. The use of urine has proven particularly suitable for quantitative analysis, because urine requires no other sample preparation apart from the alkalization and treatment thereof with activated carbon and thus can be used for the analytical determination according to the present invention. Enrichment of the acetylcyanamide, by extraction from the solution thereof, may also be necessary when the concentration is low. If the intention is to determine cyanamide in plants or microorganisms by the process of the present invention, it is possible, after the customary maceration of the cell material and after separation into solid and liquid fractions, to carry out an acetylation in the liquid in order to convert any cyanamide which is present therein into acetylcyanamide. Acetylcyanamide can be determined in the sample solution prepared in this way.

The derivatization of the cyanamide in solutions from plants or microorganisms or else from human or animal cell tissue is carried out by known methods in alkaline solution using acetic anhydride in aqueous/ethereal phase. Of course, it is also possible to apply the analytical method to the solutions of other origin containing acetylcyanamide.

According to the present invention, a matrix, which can be, for example, the metabolic product urine, or which has been subjected to a treatment to obtain an aqueous solution of acetylcyanamide, is adjusted to Ph 7.5 to 13 by addition of aqueous alkali. A preferred embodiment of the determination method comprises adjusting to a pH of 11 to 11.5 using a 20 percent sodium hydroxide or potassium hydroxide solution. For purification and clarification the alkaline solution is treated with activated carbon, and solids are removed by filtration through a membrane filter. If the concentration of acetylcyanamide in the solution is above 1 mg/kg it is suitable directly for the analytical determination by high performance liquid chromatography and spectrophotometric detection, or it is adjusted to the desired analytical concentration by dilution with water. Solutions whose acetylcyanamide content is below 1 mg/kg are acidified to pH 0.5 to 3.5 with mineral acid. For the subsequent treatment of the analytical sample, the pH is preferably adjusted to between 1.0 and 2.0 by addition of sulfuric acid or phosphoric acid. Of course, also suitable for the acidification are hydrochloric acid and other hydrohalic acids. Analytical samples in which the concentration of acetylcyanamide is below 1 mg/kg are subjected to liquid/liquid extraction for the enrichment. Suitable as solvent for this extraction are organic solvents which are insoluble in water and in which acetylcyanamide is readily soluble. Esters such as ethyl acetate or ethers such as diethyl ether have proven advantageous in this respect. The manner of the extraction can be by simple repeated extraction by shaking or continuously in an extraction apparatus.

It is possible, for further enrichment of the acetylcyanamide, to extract the organic solvent with a weakly alkaline aqueous solution. The extraction can be carried out by the customary methods by repeated extraction by shaking. Particularly suitable in practice for transferring the acetylcyanamide from the organic into the aqueous phase has proven to be not only aqueous alkali metal hydroxides but also aqueous solutions of alkali metal salts of weak acids such as, for example, sodium carbonate or sodium bicarbonate. To adjust to a concentration suitable for the determination, the aqueous extract is evaporated to dryness under mild conditions and dissolved in a defined amount of water, so that the concentration of acetylcyanamide is approximately 1 mg/kg. The mobile phase used in the subsequent ion chromatographic separation, preferably using an AS-3 separation column commercially available from Dionex, is a solution of salts of carbonic acid. For the separation of acetylcyanamide on an ion exchange phase preferably an aqueous mixture of sodium carbonate and sodium bicarbonate is used. However, it is also possible to carry out the liquid chromatography of the acetylcyanamide on a reverse phase. An example of a suitable separation column is Nucleosil 5 u C-18, 250×4.6 from Macherey and Nagel. Suitable as mobile phase is a customary phosphate buffer of pH 6.8 with tetrabutylammonium hydrogen sulfate in a methanol/water mixture.

To determine acetylcyanamide in a complex matrix such as, for example, urine, it is necessary to use two separation columns (5 and 6) connected in series. For the separation preferably a column switching technic is used as depicted in FIG. 1. In FIG. 1, (3) represents a reservoir which contains the mobile phase. Pump (1) delivers, in position (11) of the switching valve (8), the mobile phase and the analytical sample which has been injected with the injection valve (4) through the separation column (5), via the backpressure device (7) to the outlet (13). In position (12) of the switching valve (8), the delivery takes place through the separation columns (5) and (6), through the suppressor (9) to the detector (10) and to the outlet (13). The pump (2) serves to deliver the mobile phase from the reservoir (3), in valve position (12) through the back-pressure device (7) and in valve position (11) through separation column (6), the suppressor (9) and the detector (10).

To determine the column switching times, initially only chromatography column (5) is connected to the ion chromatograph, and a sodium acetylcyanamide standard is loaded on. The times at the start ($t_1$) and at the end ($t_2$) of the acetylcyanamide signal are determined. For analysis the separation columns (5 and 6) and the backpressure device (7) are installed in accordance with the arrangement in FIG. 1, and the prepared samples or standard solutions are injected. The switching valve (8) is switched at each of the times ($t_1$) and ($t_2$).

If a matrix contains only small amounts of interfering substances, the determination can be carried out with only one separation column.

Figure 2:
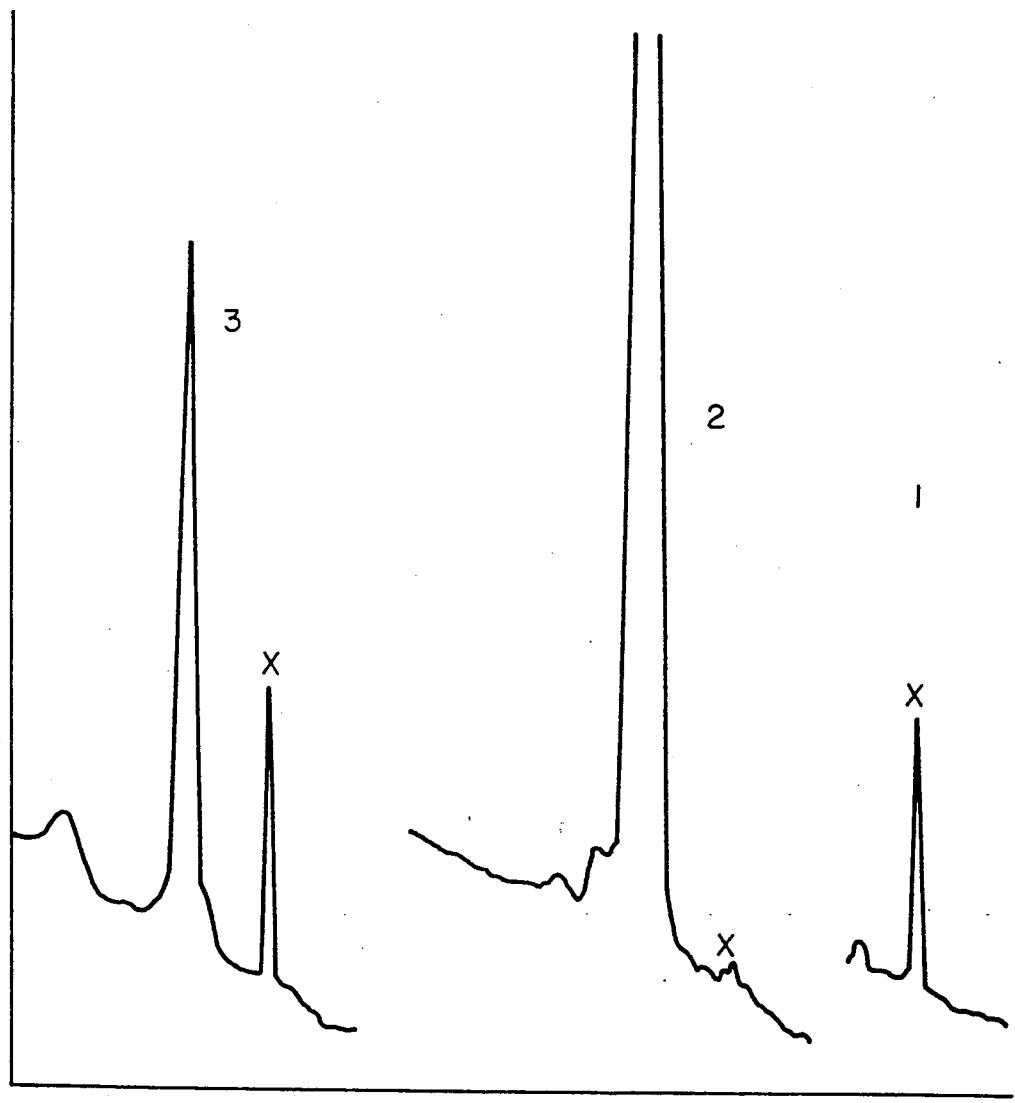

FIG. 2 represents ion chromatograms of acetylcyanamide recorded at a wavelength of 220 nm and shows the high sensitivity of the analytical method according to the present invention.

Peak X in chromatogram 1 derives from an acetylcyanamide standard, the blank sample in chromatogram 2 shows virtually no acetylcyanamide signal, and chromatogram 3 shows the result for a sample of human urine analyzed by the method of the present invention.

The highly specific and sensitive analytical method proved satisfactory even in the presence of interfering substances, as detectable by large peaks in chromatograms 2 and 3. The lower limit of determination for acetylcyanamide is below 10 ug/kg. The lower limit of determination was calculated taking 10 times of the standard deviation of the signals of urine samples spiked with 20 ppb acetylcyanamide.

Conditions for the chromatography:
A) Ion Exchange phase
   Column arrangement as in FIG. 1
   Separation column (5, 6): AS-3 Dionex
   Ion chromatograph: Dionex 2010 i
   Suppressor for the anion chromatography (9): Dionex
   Integrator: SP 4290 or equivalent
   Detector: (10): UV Kontron Uvikon 720 LC or equivalent
   Wavelength: 220 nm
   Mobile phase aqueous sodium carbonate 0.0044 mol/l, aqueous sodium bicarbonate 0.0056 mol/l in the ratio 1:1 by volume
   Injection volume: 10–100 ul
   Flow rate: 2.0 to 2.3 ml/min.
B) Reverse phase
   HPLC: Beckmann System Gold or equivalent
   Separation column: Nucleosil 5 u C-18, 250×4.6; Macherey and Nagel or equivalent
   Integrator: SP 4290 or equivalent
   Detector (10): UV Contron Uvikon 720 LC or equivalent
   Wavelength: 220 nm
   Mobile phase: 120 ml of methanol, 600 ml of water, 80 ml of phosphate buffer pH 6.8, 220 mg of tetrabutylammonium bisulfate
   Injection 10 to 100 ul
   Flow rate: 0.8 to 1.2 ml/min.

EXAMPLES

Example 1

Determination of acetylcyanamide in concentrations >1 mg/kg.

A urine sample is diluted with deionized water to approximately 1 mg/l acetylcyanamide. 150 ml of this solution are adjusted to pH 11 to 11.5 using a 20% sodium hydroxide solution. 2.5 to 3 g activated carbon are added. The sample for analysis is stirred at room temperature for 30 minutes and separated from the activated carbon by filtration through a 0.45 um membrane filter. The activated carbon is washed with 25 ml of 0.01 M sodium hydroxide solution, and the filtrate and washings were combined and made up to 200 ml with deionized water.

Determination of the column switching times for ion chromatographic analysis.

A standard of approximately 20 mg of the sodium salt of acetylcyanamide in 1000 ml of water is used. This standard is diluted 1 : 10 with water, and 50 ul of this are injected onto the separation column (5) which is connected to the ion chromatograph. The times at the start ($t_1$) and the end ($t_2$) of the acetylcyanamide signal are measured.

Measurement of the sample.

For analysis of a urine sample all parts shown in the switching plan (FIG. 1) are connected. 50 ul of the prepared urine sample are injected, and the switching valve is switched at times ($t_1$) and ($t_2$). The flow rate of the mobile phase is 2.0 to 2.3 ml/min. The concentration of acetylcyanamide is detected at a wavelength of 220 nm.

The measurement is repeated several times, injecting standard and the urine samples alternatively.

Calculation:

The acetylcyanamide concentration is calculated using the following equation $$\text{ppm Acy} = \frac{CS \times 0.793 \times f \times HPr}{HS}$$

ppm Acy = concentration of acetylcyanamide
CS = concentration of sodium acetylcyanamide in the standard
F = dilution or concentration factor for the sample solution
HPr = peak height or peak area of the sample
HS = peak height or peak area of the standard

EXAMPLE 2

Determination of acetylcyanamide in concentrations <1 mg/kg.

150 ml of a urine sample are adjusted to pH 11 to 11.5 with a 20% sodium hydroxide solution. Any white precipitate which occurs is ignored. The solution is stirred with 2.5 to 3 g of activated carbon for 30 minutes and then separated from the activated carbon by filtration through a 0.45 um membrane filter. The treatment with activated carbon is repeated twice and then the latter is washed twice with 5 ml of 0.01 M sodium hydroxide solution each time, and the combined filtrates are adjusted to pH 1.3 to 1.4 with sulfuric acid. Exactly 100 ml of this solution are extracted three times with 100 ml of ethyl acetate in each case.

The combined ethyl acetate phases are extracted three times with 5 ml of 0.05 M aqueous sodium carbonate solution in each case, and the aqueous solutions are combined and evaporated to dryness in vacuo on a rotary evaporator at a maximum temperature of 40° C.

The residue is dissolved in 10 ml of deionized water and, if necessary, diluted with deionized water to an acetylcyanamide concentration of approximately 1 mg/l. 50 ul of this solution are injected onto the ion chromatographic system. Determination and calculation are carried out in analogy to Example 1.

EXAMPLE 3

Derivatization of cyanamide to acetylcyanamide.

Approximately 10 ml of a solution containing cyanamide are alkalized using 4 ml of 40% sodium hydroxide solution, and 10 ml diethyl ether is placed on top of the solution. 1 ml acetic anhydride in 10 ml diethyl ether is added, and the mixture is shaken at room temperature for one hour. The diethyl ether is stripped off on a rotary evaporator, and the remaining aqueous solution, whose pH should be approximately 11.5, is stirred with 2 g of activated carbon for 30 minutes. The activated carbon is filtered off, washed twice with 5 ml of 0.01 M sodium hydroxide solution in each case, and the combined aqueous phases are adjusted to pH 1 with 50% concentrated sulfuric acid.

The acidic solution is processed as described in Example 2 and chromatographed, e.g. using ion chromatography and determined spectrophotometrically at a wavelength of 220 nm.

Obviously, numerous modifications and variations of the present invention are possible in light of the above teachings. It is therefore understood that within the scope of the appended claims, the invention may be practiced otherwise than as specifically described herein.

What is claimed is:

1. A process for the analytical determination of acetylcyanamide in urine comprising:
   (a) separating the acetylcyanamide in a sample from one of a purified urine matrix and an extract which is obtained from a purified urine matrix by passing said sample, without derivatisation of said acetylcyanamide, through a first column, separating a first fraction of said acetylcyanamide from the eluent of said first column, and passing the first column fraction through a second ion chromatography column; and
   (b) detecting the acetylcyanamide in the eluent of said second column fraction by spectrophotometry at a wavelength of 220 nm.

2. The process of claim 1 further comprising: prior to said separation, converting cyanamide in said sample into acetylcyanamide by a reaction with acetic anhydride.

3. The process of claim 1 further comprising:
   prior to said separation, cleaning of the matrix or the extract with activated carbon at a Ph between 7 and 13.

4. The process of claim 1 further comprising: wherein said separation is performed by reverse phase HPLC.

5. The process of claim 4 further comprising: prior to said separation, converting cyanamide in said sample into acetylcyanamide by a reaction with acetic anhydride.

6. The process of claim 1 further comprising:
   wherein said separation is performed by a liquid-liquid extraction performed between a Ph of 0.5 and 3.5.

7. The process of claim 6 further comprising: wherein said extraction is performed using a water-insoluble organic solvent.

8. The process of claim 7 further comprising: wherein said organic solvent is ethyl acetate or diethyl ether.

* * * * *